(12) United States Patent
Jones et al.

(10) Patent No.: US 10,688,248 B2
(45) Date of Patent: Jun. 23, 2020

(54) INJECTION DEVICE

(71) Applicant: Sanofi, Paris (FR)

(72) Inventors: Matthew Jones, Warwick (GB); Simon Lewis Bilton, Leamington Spa (GB)

(73) Assignee: Sanofi, Paris (FR)

(*) Notice: Subject to any disclaimer, the term of this patent is extended or adjusted under 35 U.S.C. 154(b) by 580 days.

(21) Appl. No.: 14/783,481

(22) PCT Filed: Apr. 8, 2014

(86) PCT No.: PCT/EP2014/056992
§ 371 (c)(1),
(2) Date: Oct. 9, 2015

(87) PCT Pub. No.: WO2014/166910
PCT Pub. Date: Oct. 16, 2014

(65) Prior Publication Data
US 2016/0051769 A1    Feb. 25, 2016

(30) Foreign Application Priority Data

Apr. 10, 2013  (EP) .................................... 13163092

(51) Int. Cl.
| | | |
|---|---|---|
| *A61M 5/315* | (2006.01) | |
| *A61M 5/20* | (2006.01) | |
| *A61M 5/31* | (2006.01) | |

(52) U.S. Cl.
CPC .......... *A61M 5/31586* (2013.01); *A61M 5/20* (2013.01); *A61M 5/3157* (2013.01);
(Continued)

(58) Field of Classification Search
CPC .......... A61M 5/31525; A61M 5/31528; A61M 5/31533; A61M 5/31545; A61M 5/3156;
(Continued)

(56) References Cited

U.S. PATENT DOCUMENTS

| | | | |
|---|---|---|---|
| 5,626,566 A | 5/1997 | Petersen et al. | |
| 2004/0267207 A1* | 12/2004 | Veasey ................... | A61M 5/24 604/208 |

(Continued)

FOREIGN PATENT DOCUMENTS

| | | |
|---|---|---|
| CN | 1780653 | 5/2006 |
| CN | 101184519 | 5/2008 |

(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.

(Continued)

*Primary Examiner* — Lauren P Farrar
*Assistant Examiner* — James D Ponton
(74) *Attorney, Agent, or Firm* — Fish & Richardson P.C.

(57) ABSTRACT

An injection device includes a housing, a resilient member adapted to provide a force necessary for ejecting a dose from the injection device, and a dose setting member operatively connected to a dose indicator which is positioned within the housing. The dose setting member and the dose indicator cooperate to set the dose to be ejected from the injection device. The dose indicator, during dose setting, is adapted to undergo a rotational movement within the housing and relative to the housing. Further, a gauge element is provided which is rotationally constrained to the housing and axially displaceable relative to the housing. The gauge element and the dose indicator form a limiter mechanism defining a maximum settable dose and/or a minimum settable dose.

21 Claims, 11 Drawing Sheets

(52) U.S. Cl.
CPC .... *A61M 5/31511* (2013.01); *A61M 5/31541* (2013.01); *A61M 5/31553* (2013.01); *A61M 5/31583* (2013.01); *A61M 2005/3126* (2013.01); *A61M 2005/3152* (2013.01); *A61M 2205/581* (2013.01); *A61M 2205/582* (2013.01)

(58) Field of Classification Search
CPC ............ A61M 5/31568; A61M 5/3157; A61M 2005/3125; A61M 5/31548; A61M 5/3155; A61M 5/31551; A61M 5/31553; A61M 2005/3126; A61M 2205/581
See application file for complete search history.

(56) References Cited

U.S. PATENT DOCUMENTS

| | | | |
|---|---|---|---|
| 2009/0137964 | A1 | 5/2009 | Enggaard et al. |
| 2009/0264828 | A1 | 10/2009 | Dette et al. |
| 2010/0274198 | A1* | 10/2010 | Bechtold ........... A61M 5/31551 604/189 |
| 2011/0077588 | A1* | 3/2011 | Hirschel ............. A61M 5/2033 604/82 |
| 2012/0277683 | A1* | 11/2012 | Moller .............. A61M 5/31551 604/189 |
| 2015/0038915 | A1* | 2/2015 | Pedersen .......... A61M 5/31553 604/207 |
| 2015/0224266 | A1* | 8/2015 | Plumptre ................ A61M 5/24 604/189 |

FOREIGN PATENT DOCUMENTS

| | | |
|---|---|---|
| EP | 1 804 858 | 10/2009 |
| RU | 2091087 | 9/1997 |
| WO | WO 2004/078241 | 9/2004 |
| WO | WO 2004/078242 | 9/2004 |
| WO | WO 2007/063342 | 6/2007 |
| WO | WO 2008/145171 | 12/2008 |
| WO | WO 2010/020311 | 2/2010 |
| WO | WO 2012/049138 | 4/2012 |
| WO | WO 2012/049139 | 4/2012 |
| WO | WO 2012/140097 | 10/2012 |

OTHER PUBLICATIONS

International Preliminary Report on Patentability in International Application No. PCT/EP2014/056992, dated Oct. 13, 2015, 5 pages.
International Search Report and Written Opinion in International Application No. PCT/EP2014/056992, dated Jul. 10, 2014, 7 pages.

\* cited by examiner

Figure 2
Figure 3
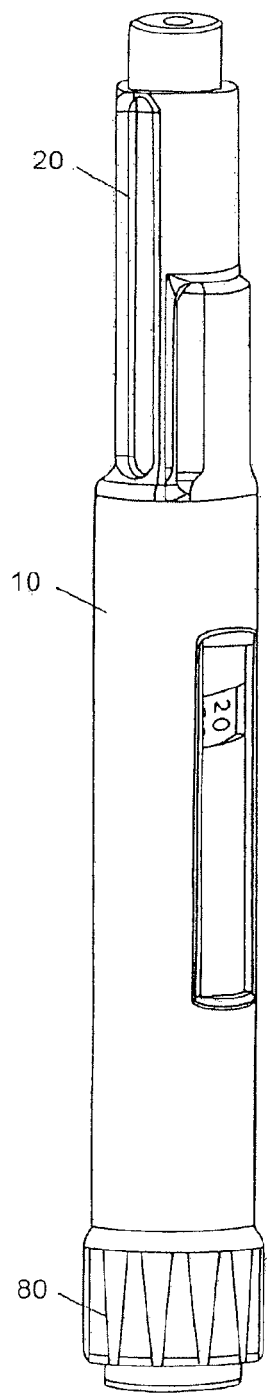
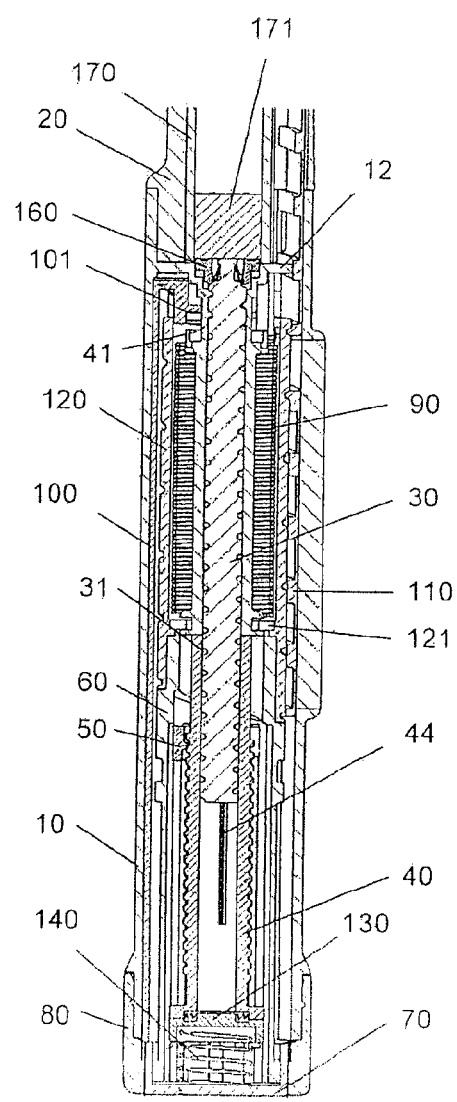

Figure 11
Figure 12
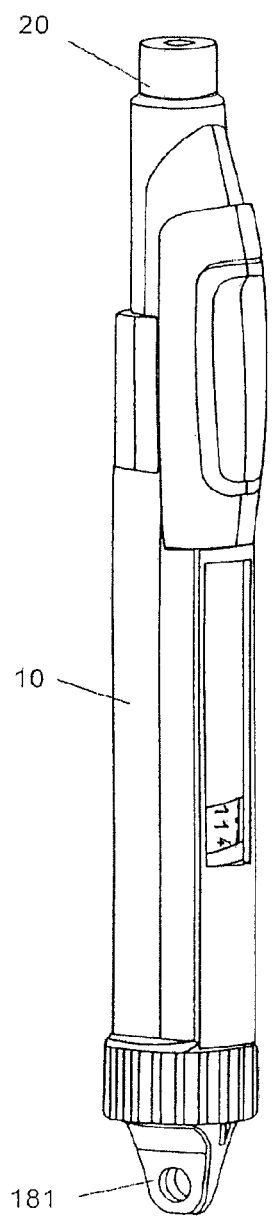
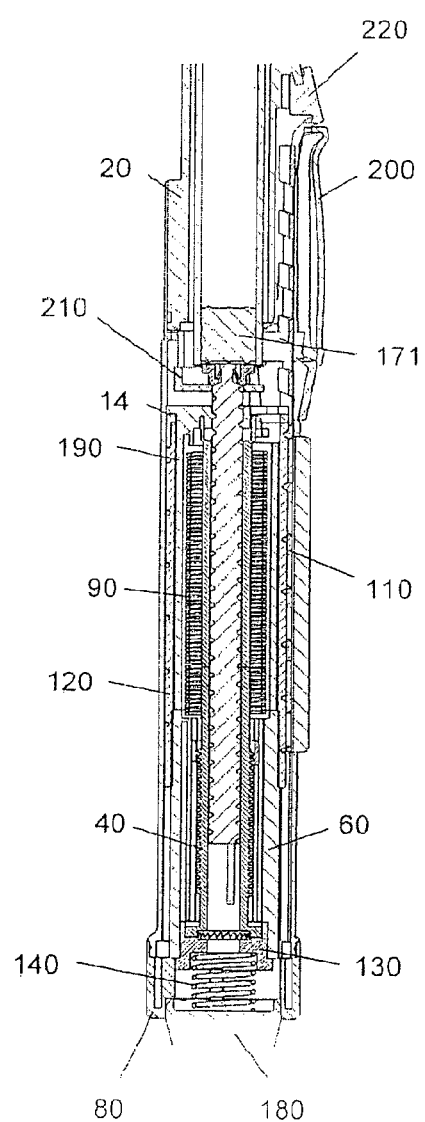

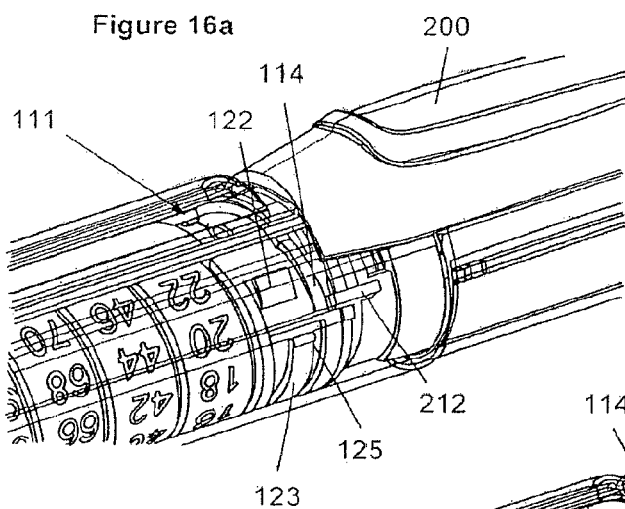
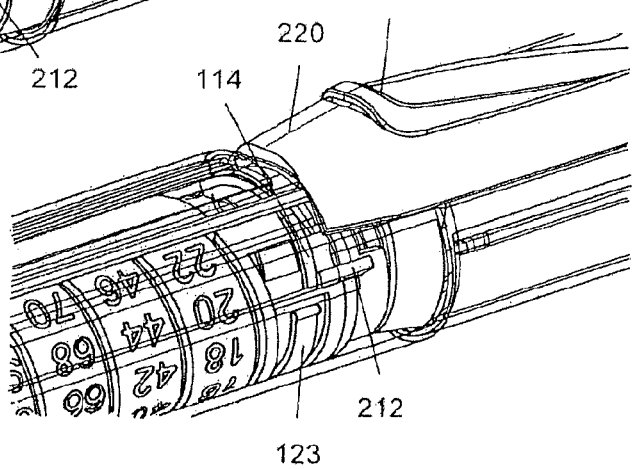
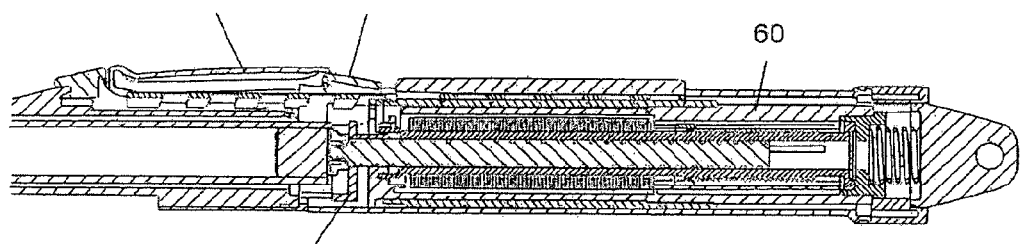
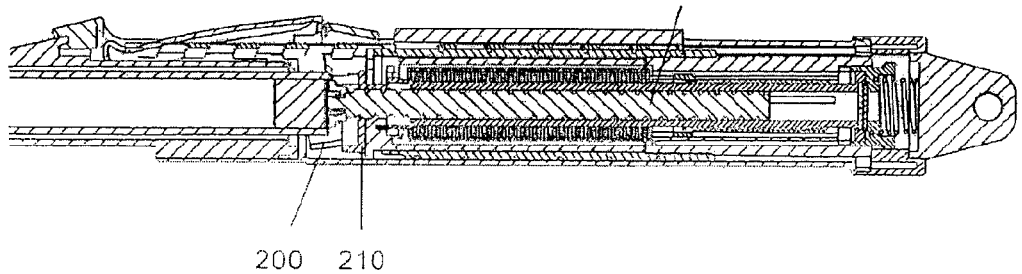

INJECTION DEVICE

CROSS-REFERENCE TO RELATED APPLICATIONS

This application is a U.S. national stage application under 35 USC § 371 of International Application No. PCT/EP2014/056992, filed on Apr. 8, 2014, which claims priority to European Patent Application No. 13163092.3, filed on Apr. 10, 2013, the entire contents of which are incorporated herein by reference.

The present invention is generally directed to an injection device, i.e. a drug delivery device for selecting and dispensing a number of user variable doses of a medicament.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present invention is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present invention is applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. In general, the present invention is applicable for all of these types of devices, i.e. for devices with or without a drive spring.

These types of pen delivery devices (so named because they often resemble an enlarged fountain pen) generally comprise of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A disposable drug delivery device for selecting and dispensing a number of user variable doses of a medicament according to the present invention typically comprises a housing, a cartridge holder for receiving a cartridge, a lead screw or piston rod and means for driving the piston rod during dose dispensing. Such a disposable drug delivery device is known from WO 2004/078241 A1, wherein the cartridge holder is rigidly attached to the device housing. The piston rod, which acts on a cartridge bung, is advanced by a driver during dose dispensing. The remaining dose in the cartridge is indicated to the user by the position of the bung and the distal end of the piston rod within the cartridge. Especially visually impaired users may find it difficult to identify the remaining dose in the cartridge.

WO 2004/078241 A1, which discloses an injection device according to the preamble of claim 1, further comprises a limiter mechanism defining a maximum settable dose with the housing being provided with a plurality of maximum dose stops adapted to be abutted by a radial stop provided on the dose dial sleeve. A similar limiter mechanism defining a minimum dose stop is provided by contact of a plurality of members extending from a dose dial grip with a corresponding plurality of stops formed in the housing.

The device of EP 1 804 858 B1 comprises a housing, a resilient member and a dose setting member operatively connected to a dose indicator barrel positioned within the housing. The resilient member is a helical spring adapted to provide a force in the axial direction of the injection device, the force being necessary for ejecting a dose from the injection device. The dose setting member and the dose indicator barrel are movable relative to each other and cooperate to set the dose to be ejected from the injection device. The dose indicator barrel engages a threaded portion of the housing. The dose indicator barrel, during dose setting, is adapted undergo a combined rotational and translational movement within the housing and relative to the housing. The combined rotational and translational movement of the dose indicator barrel is caused by its threaded interface with the housing. Generally, a translational movement of a dose indicator barrel during dose setting either results in the indicator barrel protruding from the housing depending on the amount of the set dose or this requires a relatively long housing, if it is preferred that the barrel is covered within the housing independent of the set dose.

Further, WO 2008/145171 A1 describes an injection device where the force necessary for ejecting a dose from the injection device is established manually, i.e. without the aid of a spring or the like. This device comprises has a housing, a first component for pressing out the injection liquid from a container and a dosing component in threaded engagement with the first component. The dosing component can rotate together with the first component relative to the housing for the purpose of selecting a desired injection dosing. Further, the dosing component is in threaded engagement with a window sleeve which moves axially within the housing and relative to the dosing component upon rotation of the dosing component. A number scale provided on the dosing component is visible through this window sleeve. A knob is provided, which is rotated during dose setting and which is simultaneously axially moved away from the housing as the window sleeve translates out of the housing during dose setting. Thus, although the dosing component does not perform a translational movement during dose setting, there is still a component (knob with window sleeve) protruding from the housing when a dose is set. A similar manually operated device is known from WO 2010/020311 A1, wherein the window sleeve is not limpid but has a structure distorting the view on the dosing component. A window in the housing has a corresponding distorting structure which may partially reverse the distorting effect of the window sleeve. This device comprises a limiter mechanism defining a maximum settable dose and/or a minimum settable dose provided by axial abutment of protrusions on the window sleeve and the boundaries of a housing apperture.

It is an object of the present invention to provide a drug delivery device having a reliable and robust limiter mechanism. It is a further object to make the drug delivery device compact in size, preferably without components translating out of the housing during dose setting.

This object is solved by a device as defined in claim 1.

According to a first embodiment of the present invention the injection device comprises a housing, a dose setting member, a dose indicator (e.g. a number sleeve) positioned within the housing and a limiter mechanism defining a maximum settable dose and/or a minimum settable dose. The dose setting member may be operatively connected to the dose indicator with the dose setting member and the dose indicator cooperating to set the dose to be ejected from the injection device. The dose indicator may be adapted to undergo a rotational movement within the housing and relative to the housing during dose setting. The device further comprises a gauge element which is rotationally constrained to the housing and axially displaceable relative to the housing. The gauge element and the dose indicator form the limiter mechanism. In other words, it is the interaction of the gauge element and the dose indicator which stops actuation of the device in a direction increasing a dose (for the maximum dose stop) or in a direction decreasing a dose (for the minimum dose stop).

Preferably, the limiter mechanism comprises a minimum dose (zero) position stop provided as the end of a helical thread on the dose display and a minimum dose (zero) position counter stop provided as the end of a helical thread on the gauge element and/or a maximum dose position stop provided as the end of a helical thread on the dose display and a maximum dose position counter stop provided as the end of a helical thread on the gauge element. For example, the dose indicator may be provided with a female thread (helical groove) having a hard stop at one or both ends and the gauge element may be provided with a (male) thread segment having a hard stop at one or both ends.

Typically, the minimum settable dose is zero (0 IU of insulin formulation), such that the limiter stops the device at the end of dose dispensing. The maximum settable dose, for example 60, 80 or 120 IU of insulin formulation, may be limited to avoid overdosage. Preferably, the limits for the minimum dose and the maximum dose are provided by hard stop features, e.g. rotational stops, which are more robust and more precise compared to axial stops as provided in WO 2010/020311 A1.

The limiter mechanism may comprise a first rotational stop on the dose indicator and a first counter stop on the gauge element, which abut in the minimum dose (zero) position. In addition or as an alternative, the limiter mechanism may comprise a second rotational stop on the dose indicator and a second counter stop on the gauge element, which abut in the maximum dose position. As the dose indicator rotates relative to the gauge element during dose setting and during dose dispensing, these two components are suitable to form a reliable and robust limiter mechanism. Further, the translational movement of the gauge element may be used to bring the respective counter stops on the gauge element in and out of the rotational path of the respective stops on the dose indicator.

To avoid misreadings of the dose indicator, the gauge element preferably shields the dose indicator such that only the number or the like symbol corresponding to the actually set dose is visible through the gauge element, whereas the further numbers or the like symbols are at least partially covered by the gauge element and, thus, not readable. Taking into account that the area of the dose indicator comprising the numbers or symbols has a length in the longitudinal direction of the device and that the gauge element travels axially with respect to the dose indicator, covering all but one number or symbol (or a few) on the dose indicator requires that the gauge element comprises shielding portions on both sides of its window or aperture. In other words, the gauge element is preferably an elongate component part, e.g. mainly extending in the longitudinal direction of the device, having the window or aperture and on both sides of the window or aperture a flange or the like shielding portion. In a preferred embodiment, the axial length of each of the flanges or shielding portions and the axial length of the window or aperture in sum are equal to the axial length of the area provided with numbers or symbols on the dose indicator. This does not exclude embodiments where the flanges or shielding portions are somewhat shorter or longer compared with the area provided with numbers or symbols on the dose indicator provided that mainly the actual set dose is visible through the window or aperture in the gauge element and all or most of the other numbers or symbols are covered.

The gauge element may be arranged within the housing in a radial position directly interposed between the housing and the dose indicator, i.e. without additional component parts interposed between either the housing and the gauge element or between the gauge element and the dose indicator.

Preferably, the window or aperture in the gauge element is limpid, i.e. it does not distort the numbers or symbols on the dose display in such a way that they are not readable. This does not exclude a magnifying effect of one or both of the windows or apertures in the housing and the gauge element. The window or aperture in the housing and the window or aperture in the gauge element preferably are each suitable to view the numbers or symbols on the dose display with or without the other window or aperture.

The dose indicator preferably has a first portion provided with a helical thread on its outer surface and a second portion being provided with numbers or symbols arranged on a helical path on its outer surface, wherein the first and second portions are located one behind the other in the longitudinal direction of the device and do not overlap. A corresponding inner thread or inner thread segment may be arranged on one of the flanges or shielding portions of the gauge element.

It is preferred if the device is suitable for dispensing variable, user-selectable, doses of medicament. The device may be a disposable device, i.e. a device which does not provide for an exchange of an empty cartridge. As a skilled person will understand, the injection device may comprise additional component parts like a piston rod. However, such component parts may significantly vary in design and function and thus may be provided independent of the present invention. Such additional component parts are not necessary for the interaction of the gauge element and the dose indicator to form the limiter mechanism nor for the interaction of the gauge element and the dose indicator with the housing and/or the dose setting member.

As the gauge element is rotationally constrained to the housing and axially displaceable relative to the housing, the position of the gauge element may be used to identify the actually set and/or dispensed dose. Different colours of sections of the gauge member may facilitate identifying the set and/or dispensed dose without reading numbers, symbols or the like on a display.

Preferably, the gauge element is in threaded engagement with the dose indicator such that rotation of the dose indicator causes an axial displacement of the gauge element relative to the dose indicator and relative to the housing. The gauge element may have the form of a shield or strip extending in the longitudinal direction of the device. As an alternative, the gauge element may be a sleeve.

The dose indicator may be adapted to undergo a mere rotational movement within the housing and relative to the housing during dose setting and during dose dispensing. In other words, the dose indicator is allowed to rotate but is axially constrained to the housing at least during dose setting and during dose dispensing. This prevents that the dose indicator is wound out of the housing or that the housing has to be prolonged for covering the dose indicator within the housing. Further, the gauge element may be adapted to undergo a mere translational movement within the housing and relative to the housing during dose setting and during dose dispensing, i.e. the gauge element is rotationally constrained to the housing but free to be displaced in an axial direction. The different movements of the gauge element and the dose indicator contribute to forming a robust and reliable dose limiter.

In an embodiment of the invention, the dose indicator, for example a number sleeve or display drum, is marked with a sequence of numbers or symbols and the gauge element comprises an aperture or window. With the dose indicator located radially inwards of the gauge element, this allows that at least one of the numbers or symbols on the dose indicator is visible through the aperture or window. In other words, the gauge element may be used to shield or cover a portion of the dose indicator and to allow view only on a limited portion of the dose indicator. This function may be in addition to the gauge element itself being suitable for identifying or indicating the actually set and/or dispensed dose.

The injection device may further comprise a resilient member, preferably a torsion spring, adapted to provide a force necessary for ejecting a dose from the injection device. Such a torsion spring may be strained during dose setting. The spring is preferably preloaded and is further strained by the user during dose setting. The stored energy is at least in part released during dose dispensing.

Preferably, the injection device further comprises a piston rod having a threaded outer surface with at least one drive track arranged in a longitudinal direction of the outer surface of the piston rod. In addition, the injection device may comprise a drive member engaging at least part of the drive track of the piston rod and being releasably coupled to the dose indicator. The drive member may be adapted to drive and rotate with the piston rod during ejection of a dose from the injection device. If the housing has a threaded portion cooperating with the threaded outer surface of the piston rod, rotation of the piston rod may result in an axial movement of the piston rod. As an alternative, the piston rod may be splined to the housing and threaded to the driver, which again causes an axial movement of the piston rod upon rotation of the driver. As a further alternative, the piston rod may be pushed in the axial direction, e.g. by a translational movement of the driver.

To prevent an underdosage or a malfunction, the drug delivery device may comprise a last dose protection mechanism for preventing the setting of a dose, which exceeds the amount of liquid left in a cartridge. In a preferred embodiment, this last dose protection mechanism only detects the medicament remaining in the cartridge when the cartridge contains less than the maximum dose (e.g. 120 IU).

For example, the last dose protection mechanism comprises a nut member located interposed between the drive member and a component which rotates during dose setting and dose dispensing. The component which rotates during dose setting and dose dispensing may be the dose indicator or a dial sleeve rotationally constrained to the dose indicator. In a preferred embodiment, the dose indicator and/or a dial sleeve rotate during dose setting and during dose dispensing, whereas the drive member only rotates during dose dispensing together with the dose indicator and/or the dial sleeve. Thus, in this embodiment, the nut member will only move during dose setting and will remain stationary with respect to these components during dose dispensing. Preferably, the nut member is threaded to the drive member and splined to the dose indicator and/or the dial sleeve. As an alternative, the nut member may be threaded to the dose indicator and/or the dial sleeve and may be splined to the drive member. The nut member may be a full nut or a part thereof, e.g. a half nut.

The sequence of dose setting and dose dispensing usually requires a relative movement of some of the components either during dose setting and/or during dose dispensing. Various different embodiments of achieving this result are possible, some of which are described in the prior art mentioned above. According to a preferred example of the invention, the injection device may further comprise a clutch arranged between the drive member and the dose indicator, wherein the clutch allows relative rotation of the drive member and the dose indicator during dose setting and rotationally constrains the drive member and the dose indicator during dose dispensing. Such a clutch may comprise a series of teeth on the drive member and corresponding clutch teeth on a separate clutch plate which is e.g. rotationally constrained to the dose indicator. If the drive member is held unrotatable during dose setting, relative rotation of the dose indicator with respect to the drive member causes this clutch to slip. Compression of a return spring may be used to increase frictional forces in the clutch helping to prevent it slipping during dispense and to ensure that the driver rotates the same amount as the dose indicator. Preferably, in addition to this, splines between the dose indicator and drive member are engaged during dispense to prevent relative rotation. Alternative embodiments may include a relative axial movement during dose setting or a joint movement during dose setting followed by a relative movement during dose dispensing.

The injection device may comprise at least one clicker mechanism for generating a tactile and/or audible feedback. Preferably, the clicker mechanism signifies the end of dose dispensing. In a preferred embodiment of the invention, the device comprises at least a first clicker producing an audible and/or tactile first feedback during dose setting and/or dose dispensing and a second clicker producing an audible and/or tactile second feedback, distinct from the first feedback, during dose dispensing when the device reaches its minimum dose (zero) position. The injection device may have different clickers active during dose setting and during dose dispensing.

Spring loaded injection devices often comprise an actuation element for releasing the energy stored in the resilient member, e.g. in the spring. Typically, the user presses or activates this actuating element after a dose has been set to initiate dose dispensing. According to a first embodiment, the actuating element may comprise a button located at the proximal end of the housing, i.e. the end facing away from the needle. As an alternative, a trigger may be provided located on a lateral side of the housing, preferably in the distal region of the device. The actuation element may act on the clutch to rotationally constrain the drive member and the dose indicator for dose dispensing.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyldes(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-GluGly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Non-limiting, exemplary embodiments of the invention will now be described with reference to the accompanying drawings, in which:

FIG. 2 shows a perspective view of the device of FIG. 1;

FIG. 3 shows a sectional view of the device of FIG. 1;

FIG. 11 shows a perspective view of the device of FIG. 10.

FIG. 12 shows a sectional view of the device of FIG. 10;

Figure 10:
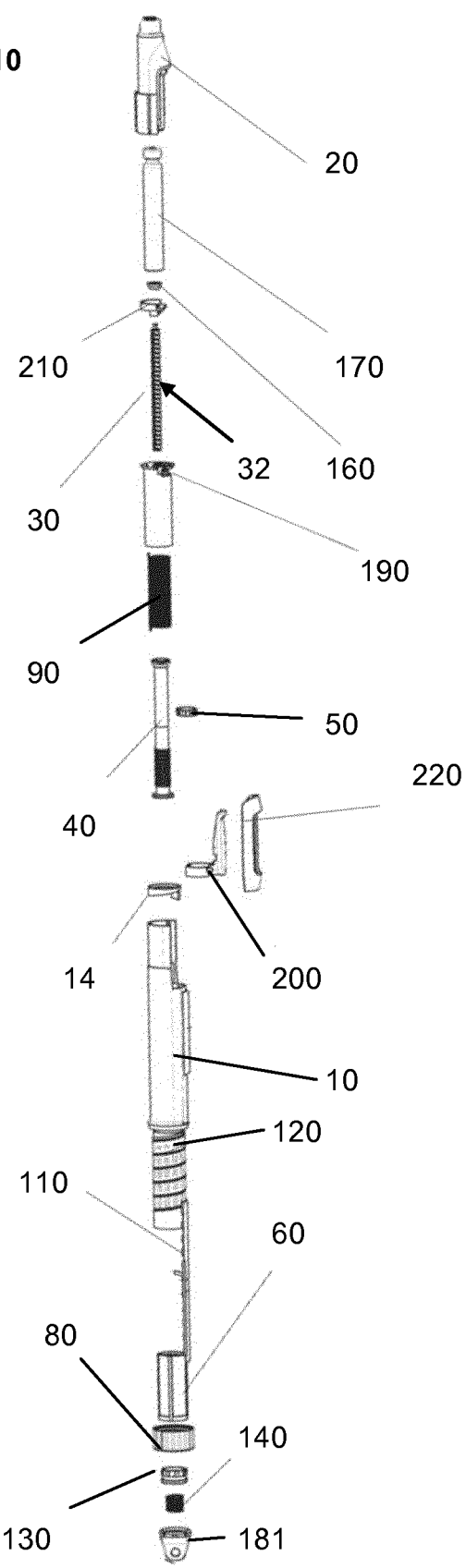
FIG. 10 shows an exploded view of the components of an injection device in accordance with a second embodiment of the present invention.
Figure 13:
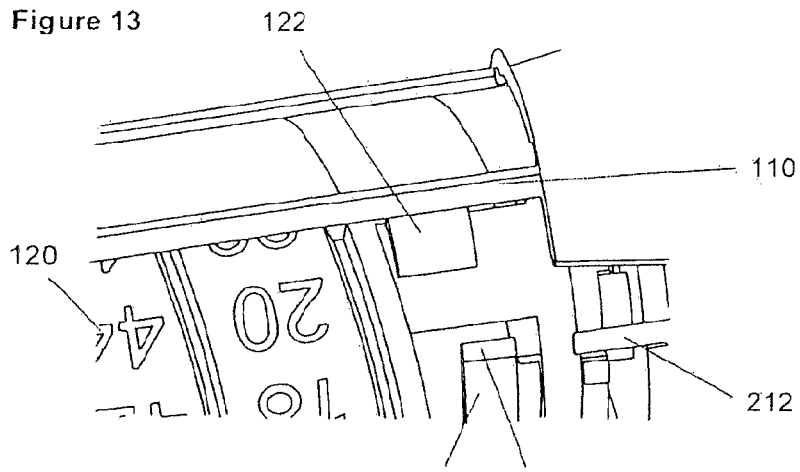
FIG. 13 shows an enlarged view of a detail of the device of FIG. 10.
Figures 15A, 15B:
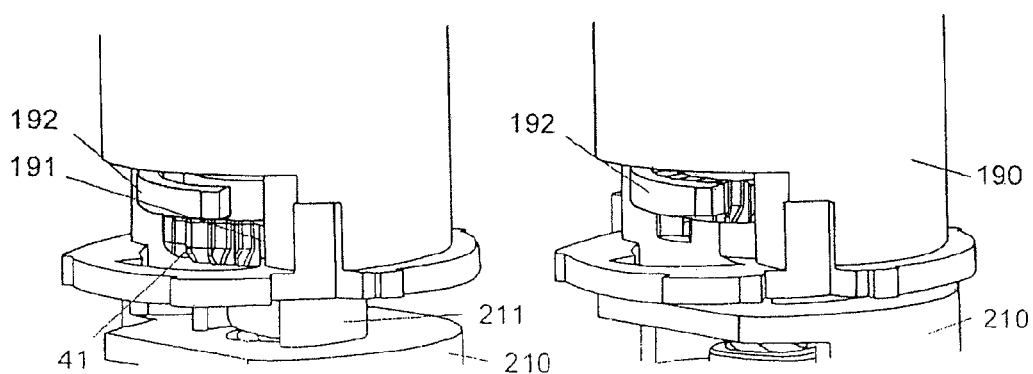

FIGS. 15a, b show an enlarged view of a detail of the device of FIG. 10;

FIGS. 16a, b show an enlarged view of a detail of the device of FIG. 10;

FIG. 17 shows a sectional view of the device of FIG. 10 in the at rest state;

FIG. 18 shows a sectional view of the device of FIG. 10 in the activated state

Figure 19:
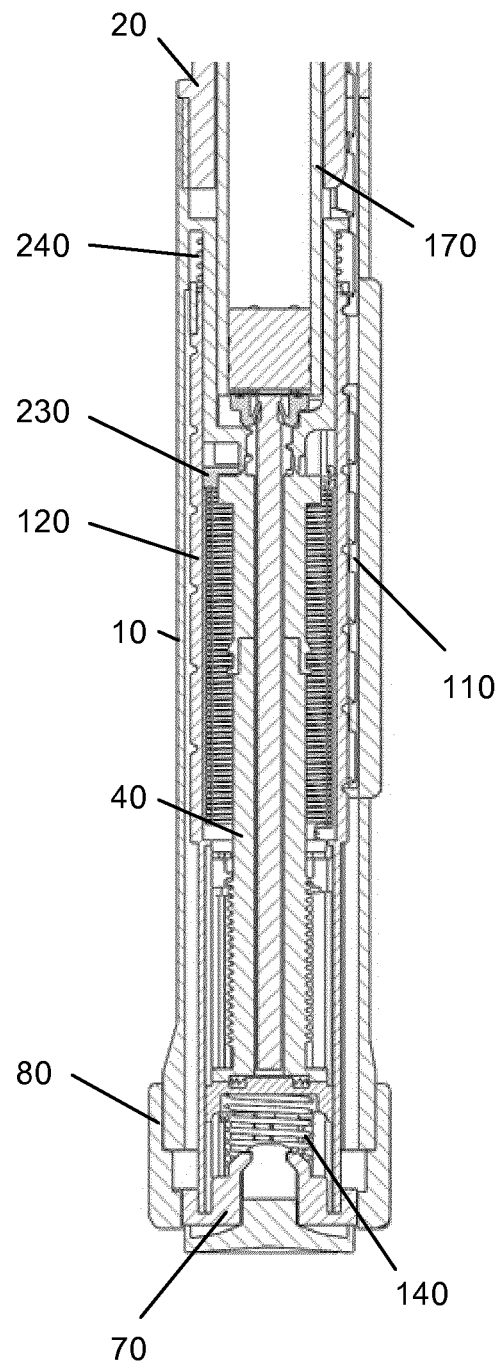
Figure 20:
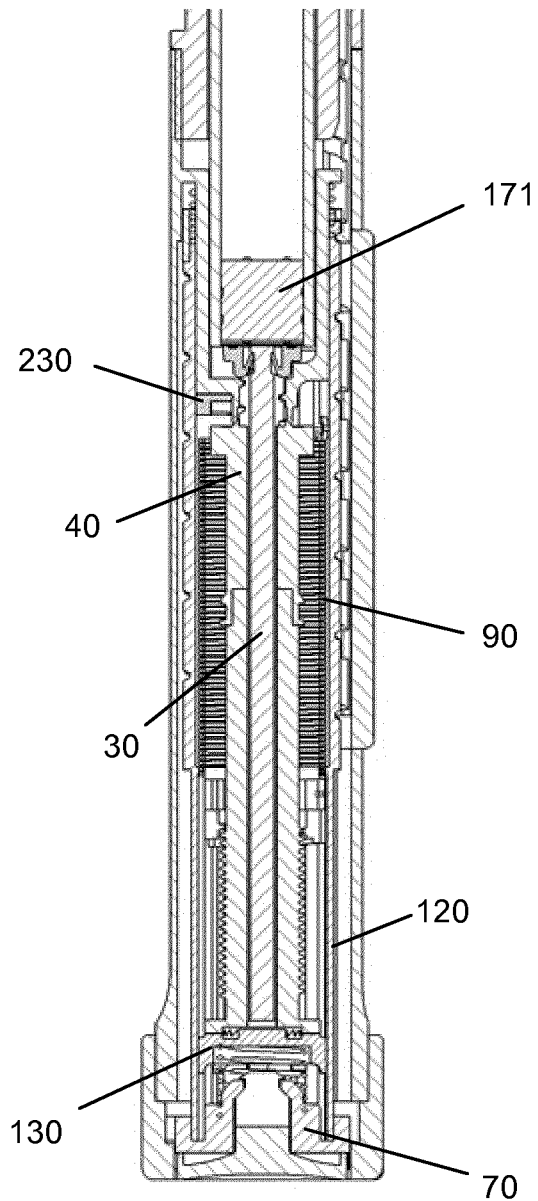
Figure 21:
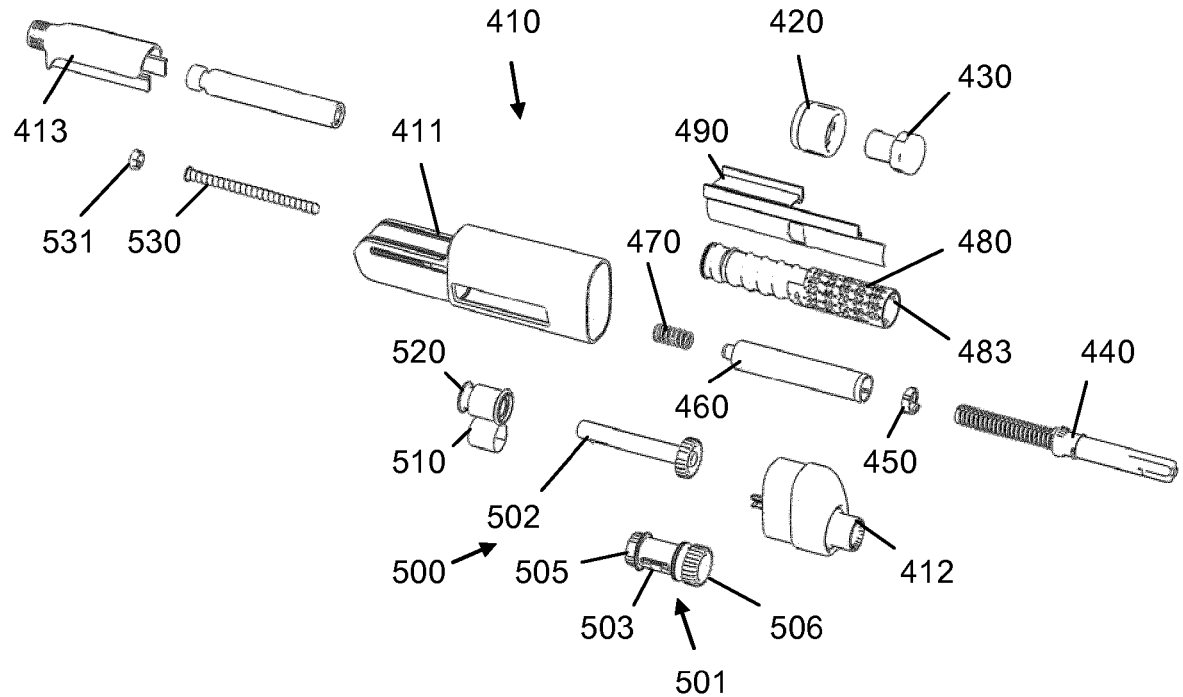
Figure 22:
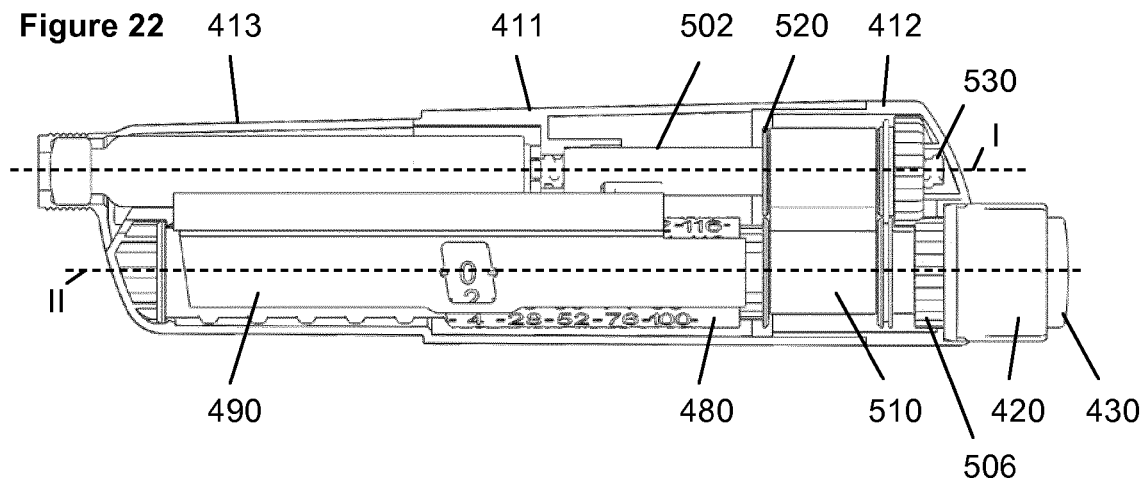

FIG. 19 shows a sectional view of an injection device in accordance with a third embodiment of the present invention in the at rest state;

FIG. 20 shows a sectional view of the device of FIG. 19 in the activated state;

FIG. 21 shows an exploded view of the components of an injection device in accordance with a fourth embodiment of the present invention; and FIG. 22 shows a partially cut away side view of the device of FIG. 21.

Figure 1:
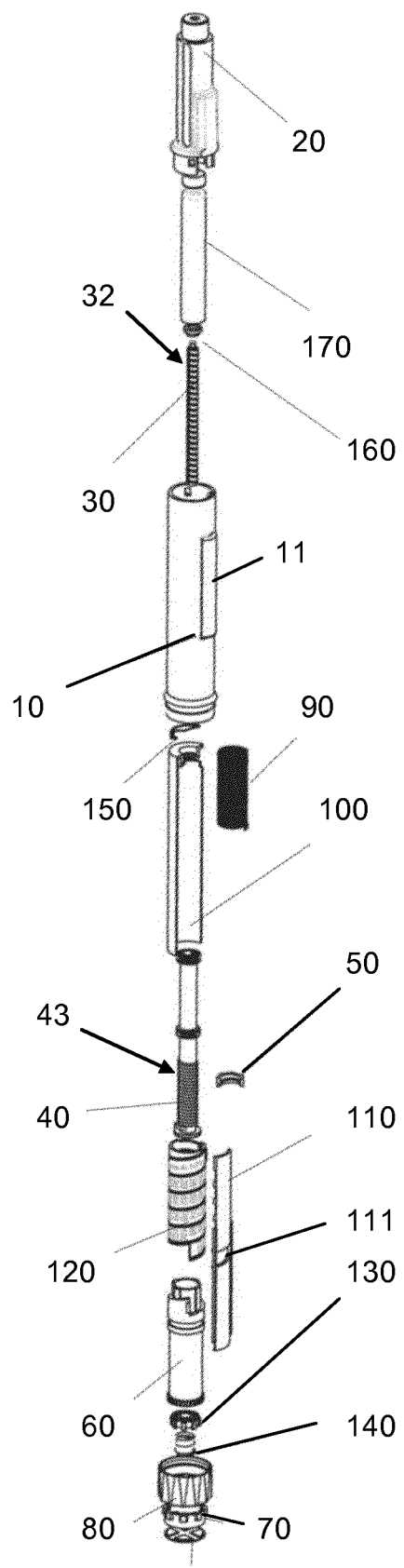
FIG. 1 shows an exploded view of the components of an injection device in accordance with a first embodiment of the present invention.

FIG. 2 shows a drug delivery device in the form of an injection pen. The device has a distal end (upper end in FIG. 2) and a proximal end (lower end in FIG. 2). The component parts of the drug delivery device are shown in FIG. 1. The drug delivery device comprises a housing 10, a cartridge holder 20, a lead screw (piston rod) 30, a driver 40, a nut 50, a dial sleeve 60, a button 70, a dose selector 80, a torsion spring 90, a locking arm 100, a gauge element 110, a dose indicator (number sleeve) 120, a clutch plate 130, a clutch spring 140, a return spring 150, a bearing 160 and a cartridge 170. A needle arrangement (not shown) with a needle hub and a needle cover may be provided as additional components, which can be exchanged as explained above.

The housing 10 or body is a generally tubular element. In the embodiment shown in the figures, the housing 10 provides location for the liquid medication cartridge 170 and cartridge holder 20, an interface to rotationally constrain the locking arm 100, a slot 11 or lens through which the dose number on the dose indicator 120 and the gauge area of the gauge element 110 that preferably covers and reveals the contrast element can be viewed, and a feature, e.g. a circumferential groove, on its external surface to axially retain the dose selector 80. A flange-like inner wall 12 comprises an inner thread engaging the piston rod 30. Further a clicker arm 13 or beam is integrated into the housing 10 for interaction with the driver 40.

The cartridge holder 20 is located at the distal side of housing 10. The cartridge holder may be a transparent or translucent component which is tubular to receive cartridge 170. The distal end (upper end in FIG. 2) of cartridge holder 20 may be provided with means for attaching a needle arrangement. A removable cap (not shown) may be provided to fit over the cartridge holder 20 and may be retained via clip features.

The lead screw 30 is an elongate member with an outer thread 31 which is rotationally constrained to the driver 40 via a splined interface. The interface comprises at least one longitudinal groove or track 32 and a corresponding protrusion or spline 44 of the driver 40. When rotated, the lead screw 30 is forced to move axially relative to the driver 40, through its threaded interface with the housing 10.

The driver 40 is a sleeve which extends from the interface with the dial sleeve 60 via the clutch plate 130 down to a splined tooth interface 41 with the locking arm 100. This provides rotational constraint of the locking arm 100 to the driver 40 during dose setting. When the dose button 70 is pressed, these spline teeth are disengaged allowing the driver 40 to rotate. Further, teeth 42 are provided at the proximal end face of driver 40 for engagement with clutch plate 130. The driver 40 has a threaded section 43 providing a helical track for the nut 50. In addition, a last dose abutment is provided which may be the end of the thread 43 track or preferably a rotational hard stop limiting movement of the nut 50 on the thread 43.

The nut 50 is part of a last dose limiter mechanism. The nut 50 is located between the dial sleeve 60 and the driver 40. It is rotationally constrained to the dial sleeve 60, via a splined interface. It moves along a helical path relative to the driver 40, via a threaded interface, when relative rotation occurs between the dial sleeve 60 and driver 40 during dialling. As an alternative, the nut 50 may be splined to the driver 40 and threaded to the dial sleeve 60. In the exemplary embodiment of FIGS. 1 to 9, the nut 50 is a half nut, i.e. a component extending approximately 180° around the center axis of the device. As a preferred alternative, for example if the driver 40 was formed from two separate components that became rigidly engaged during assembly, the nut 50 could also be a complete nut.

The dial sleeve 60 is a tubular element. It receives the clutch plate 130 and the proximal end of the driver 40 to which it may be coupled via the clutch plate. The distal end of the dial sleeve 60 is permanently constrained to the dose indicator 120. For manufacturing reasons, the dial sleeve 60 and the dose indicator 120 are separate components. However, they could be integrated into a single component part. In this embodiment, the dose indicator 120 and dial sleeve 60 act as a single part after assembly.

According to a preferred alternative, the arrangement is similar with the dose indicator 120 being formed from an upper and lower part, which may act as a single part after assembly.

Functions of the dose indicator 120 as described herein may be achieved by either the upper or lower dose indicator. Also, functions of the dial sleeve 60 may be achieved by either the upper or lower part of such a split dose indicator.

Figure 6:
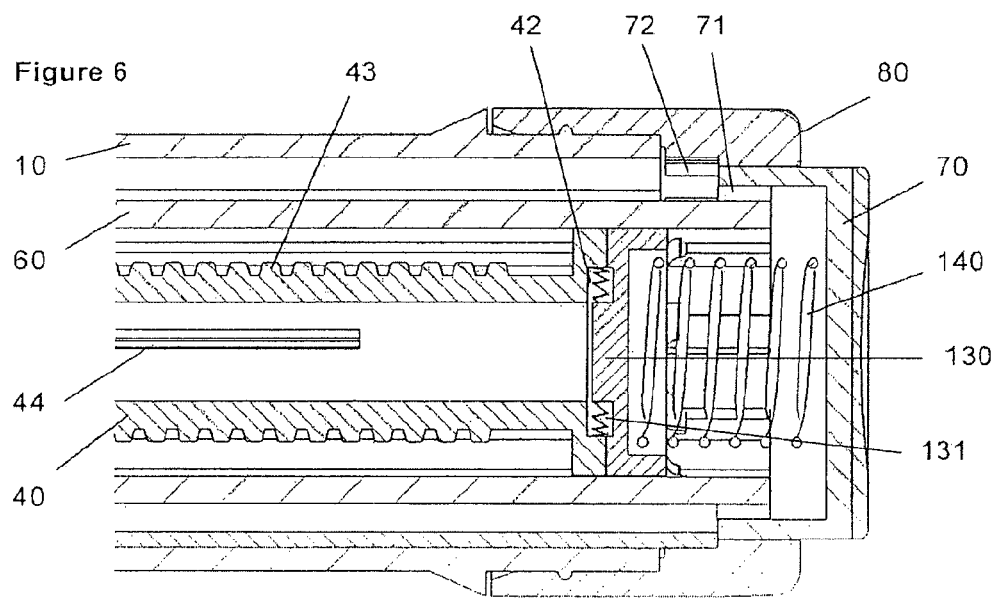
FIG. 6 shows an enlarged sectional view of a detail of the device of FIG. 1.

The button 70 forms the proximal end of the device. Button 70 has an annular skirt received within dose selector 80. Further, button 70 has a proximal end plate onto which a button cover may be placed as indicated in FIG. 1. The dose button 70 is permanently splined to the dose selector 80 and splined to the dial sleeve 60 by respective spline features 71, 72 when the button 70 is not pressed. This spline interface 71, 72 is disconnected when the dose button 70 is pressed. Dose dispensing is initiated by actuation of the dose button 70. FIG. 6 shows the spline features 72 as teeth and spline features 71 of the button skirt may be designed in a similar manner such that these teeth 71, 72 are allowed to engage or disengage corresponding teeth on the inner surface of dose selector 80 and the outer surface of dose dial sleeve 60, respectively.

The dose selector 80 or dose dial grip is a sleeve-like component with a serrated outer skirt. The dose selector 80 is axially constrained to the housing 10. It is rotationally constrained, via the splined interface, to the dose button 70. This splined interface remains engaged irrespective of the dose button 70 axial position.

The torsion spring 90 is attached at one end to the housing 10 and at the other end to the dose indicator 120. The torsion spring 90 is pre-wound upon assembly, such that it applies a torque to the dose indicator 120 when the mechanism is at zero units dialled. The action of rotating the dose selector 80, to set a dose, rotates the dose indicator 120 relative to the housing 10, and charges the torsion spring 90. The torsion spring 90 is located inside the dose indicator 120 and surrounds a distal portion of the driver 40.

The locking arm 100 is rotationally fixed to the housing 10 but allowed to translate axially. Axial movement is effected by the dose button 70 which abuts with its distal face the proximal face of the locking arm 100. Near its distal end, the locking arm 100 has teeth 101 for releasably coupling the tooth interface 41 of driver 40 to the housing 10 via the locking arm 100.

The gauge element 110 is a window element which is constrained to prevent rotation but allow translation relative to the housing 10 via a splined interface. It is also in threaded engagement to the dose indicator 120 such that rotation of the dose indicator 120 causes axial translation of the gauge element 110. The gauge element 110 has helical cuts in its inner surface which provide clearance for stop features on the dose indicator 120 as the gauge element 110 traverses axially during number sleeve rotation. The gauge element 110 is positioned in housing 10 such that it is guided within slot 11 and closes same. It is a generally plate or band like component having a central aperture 111 or window and two flanges 112, 113 extending on either side of the aperture. The flanges 112, 113 are preferably not transparent and thus shield or cover the dose indicator 120, whereas the aperture 111 or window allows viewing a portion of the number sleeve. Further, gauge element 110 has an arm 114 interacting with the dose indicator 120 at the end of dose dispensing. The gauge element 110 is shown in more detail in FIGS. 5a to 5c together with dose indicator 120.

The dose indicator 120 is a number sleeve which is rotationally constrained, via a splined interface, to the dial sleeve 60. They are constrained to the housing 10 to allow rotation but not translation. The dose indicator 120 is marked with a sequence of numbers, which are visible through the central aperture 111 in the gauge element 110 and a slot 11 in the housing 10, to denote the dialled dose of medicament. A lock ring 121 may be rigidly constrained to the dose indicator 120. This ring is only a separate component to simplify the number sleeve mould tooling. The dose indicator 120 has a ramp-like rotational stop 122 abutting against a lateral side of the gauge element 110 in a position, where a dose of zero units is dialled (minimum dose position). A similar stop 122' is provided on the opposite side of the dose indicator 120 to prevent setting of a dose above the maximum dose, e.g. above 120 units. In a preferred embodiment, the stop features are formed at the ends of the thread in the dose indicator 120, interacting with the ends of the thread on the gauge element 110. A flexible arm 123 is provided interacting with the arm 114 of the gauge element 110 at the end of dose dispensing. In the embodiments of FIGS. 1 to 20, the dose indicator comprises a thread overlapping the area of its outer surface comprising numbers or the like symbols. In an alternative embodiment, the dose indicator may have a configuration similar to that of FIG. 21 where the dose indicator has a first portion provided with a helical thread on its outer surface and a second portion being provided with numbers or symbols arranged on a helical path on its outer surface, with the first and second portions being located one behind the other in the longitudinal direction of the device and do not overlap.

The clutch plate 130 is splined to the dial sleeve 60. It is also coupled to the driver 40 via a ratchet interface 42, 131, which occurs on an axial abutment. The ratchet 42, 131 provides a detented position between the dial sleeve 60 and driver 40 corresponding to each dose unit, and engages different ramped tooth angles during clockwise and anti-clockwise relative rotation. FIG. 6 shows the clutch plate 130 together with the proximal end of the device in more detail.

The clutch spring 140 is located interposed between button 70 and clutch plate 130. It acts on the clutch plate allowing the ratchet teeth 42, 131 to bump over each other during dose setting against the axial force of the spring.

The return spring 150 acts against the locking arm 100 to force the spline teeth 101 into engagement with the teeth 41 of driver 40.

The bearing 160 is axially constrained to the lead screw 30 and acts on the bung within the liquid medicament cartridge 170.

The cartridge 170 is received in cartridge holder 20. The cartridge 170 may be a glass ampoule having a moveable rubber bung 171 at its proximal end. The distal end of cartridge 170 is provided with a pierceable rubber seal which is held in place by a crimped annular metal band. In the embodiment depicted in the figures, the cartridge 170 is a standard 1.5 ml cartridge. The device is designed to be disposable in that the cartridge 170 cannot be replaced by the user or health care professional. However, a reusable variant of the device could be provided by making the cartridge holder 20 removable and allowing backwinding of the lead screw 30 and the resetting of nut 50.

The axial position of the locking arm 100, clutch plate 130 and dose button 70 is defined by the action of the return spring 150 and clutch spring 140, which apply a force on the locking arm 100 and dose button 70 in the proximal direction. In the "at rest" position (shown in FIG. 2), this ensures that the dose button 70 splines are engaged with the dial sleeve 60 and that the driver 40 teeth 41 are engaged with the locking arm 100.

In the following, the functioning of the disposable drug delivery device and its components will be explained in more detail.

When the device is at rest as shown in FIG. 2, the dose indicator 120 is positioned against its zero dose abutment (FIG. 4) with the gauge element 110 and the dose button 70 is not depressed. Dose marking '0' on the dose indicator 120 is visible through the window of the housing 10 and the central aperture 111 in the gauge element 110. The torsion spring 90, which has a number of pre-wound turns applied to it during assembly of the device, applies a torque to the dose indicator 120 and is prevented from rotating by the zero dose abutment 122. It might also be possible to "back-wind" the mechanism slightly due to an offset between the zero dose stop 122 and the angular offset of the driver 40 spline teeth 41. This has the effect of preventing possible weepage when a dose is dialled and the zero dose abutment is disengaged.

The user selects a variable dose of liquid medicament by rotating the dose selector 80 clockwise, which generates an identical rotation in the dial sleeve 60 and hence dose indicator 120. Rotation of the dose indicator 120 causes charging of the torsion spring 90, increasing the energy stored within it. As the dose indicator 120 rotates, the gauge element 110 translates axially due to its threaded engagement thereby showing the value of the dialled dose. In a preferred embodiment, there is only one portion of thread on the gauge element 110. As mentioned above, the gauge element 110 has flanges 112, 113 either side of the central aperture 111 which may have visual differentiation to provide additional feedback to the dialled/delivered dose value. Central aperture 111 shows both the gauge area that covers and reveals the contrast element and also shows the dose number. The embodiment of FIGS. 1 to 9 utilises a dose selector 80 with an increased diameter relative to the housing 10 which aids dialling. The driver 40 is prevented from rotating, due to the engagement of its splined teeth 41 with the locking arm 100. Relative rotation must therefore occur between the clutch plate 130 and driver 40 via the ratchet interface 42, 131.

The user torque required to rotate the dose selector 80 is a sum of the torque required winding up the torsion spring 90, and the torque required overhauling the ratchet feature 42, 131. The clutch spring 140 is designed to provide an axial force to the ratchet feature and to bias the clutch plate 130 onto the driver 40. This axial load acts to maintain the ratchet teeth engagement of the clutch plate 130 and driver 40. The torque required to overhaul the ratchet 42, 131 is resultant from the axial load applied by the clutch spring 140, the clockwise ramp angle of the ratchet 42, 131, the friction coefficient between the mating surfaces and the mean radius of the ratchet features.

As the user rotates the dose selector 80 sufficiently to increment the mechanism by 1 unit, the dial sleeve 60 rotates relative to the driver 40 by 1 ratchet tooth. At this point the ratchet teeth 42, 131 re-engage into the next detented position. An audible click is generated by the ratchet re-engagement, and tactile feedback is given by the change in torque input required.

Relative rotation of the dial sleeve 60 and the driver 40 also causes the nut 50 to travel along its threaded path, towards its last dose abutment on the driver 40.

With no user torque applied to the dose selector 80, the dial sleeve 60 is now prevented from rotating due to the action of the torque applied by the torsion spring 90, solely by the ratchet 42, 131 engagement between the clutch plate 130 and the driver 40. The torque necessary to overhaul the ratchet 42, 131 in the anti-clockwise direction is resultant from the axial load applied by the clutch spring 90, the anti-clockwise ramp angle of the ratchet, the friction coefficient between the mating surfaces and the mean radius of the ratchet features. The torque necessary to overhaul the ratchet 42, 131 must be greater than the torque applied to the dial sleeve 60 and hence clutch plate 130 by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interfaces between the dial sleeve 60 and driver 40 is repeated for each dose unit. Additional energy is stored within the torsion spring 90 for each dose unit and audible and tactile feedback is provided for each unit dialled by the re-engagement of the ratchet teeth 42, 131. The torque required to rotate the dose selector 80 increases as the torque required to wind up the torsion spring 90 increases. The torque required to overhaul the ratchet 42, 131 in the anticlockwise direction must therefore be greater than the torque applied to the dial sleeve 60 by the torsion spring 90 when the maximum dose has been reached.

If the user continues to increase the selected dose until the maximum dose limit is reached, the dose indicator 120 engages with its maximum dose abutment on the gauge element 110. This prevents further rotation of the dose indicator 120, dial sleeve 60, clutch plate 130 and dose selector 80. Depending on how many units have already been delivered by the mechanism, during selection of a dose, the nut 50 may contact its last dose abutment with the driver 40. The abutment prevents further relative rotation of the dial sleeve 60 and the driver 40, and therefore limits the dose that can be selected. The position of the nut 50 is determined by the total number of relative rotations between the dial sleeve 60 and driver 40, which have occurred each time the user sets a dose.

With the mechanism in a state in which a dose has been selected, the user is able to deselect any number of units from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet 42, 131 between the clutch plate 130 and driver 40 in the anti-clockwise direction. When the ratchet is overhauled, anti-clockwise rotation occurs in the dial sleeve 60 via the clutch plate 130, which returns the dose indicator 120 towards the zero dose position, and unwinds the torsion spring 90. The relative rotation between the dial sleeve 60 and driver 40 causes the nut 50 to return along its helical path (thread 43), away from the last dose abutment on the driver 40.

Figure 7:
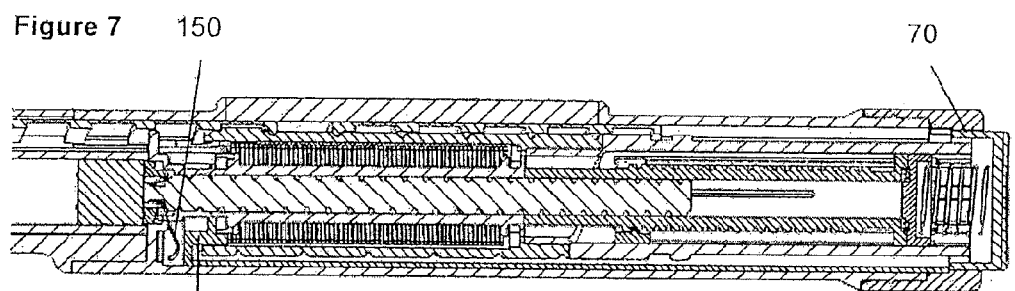
FIG. 7 shows a sectional view of the device of FIG. 1 in the at rest state.
Figure 8:
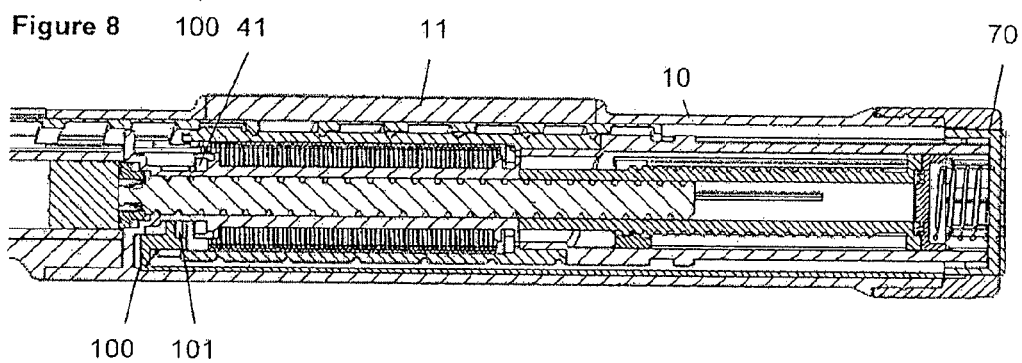
FIG. 8 shows a sectional view of the device of FIG. 1 in the activated state.
Figure 9:
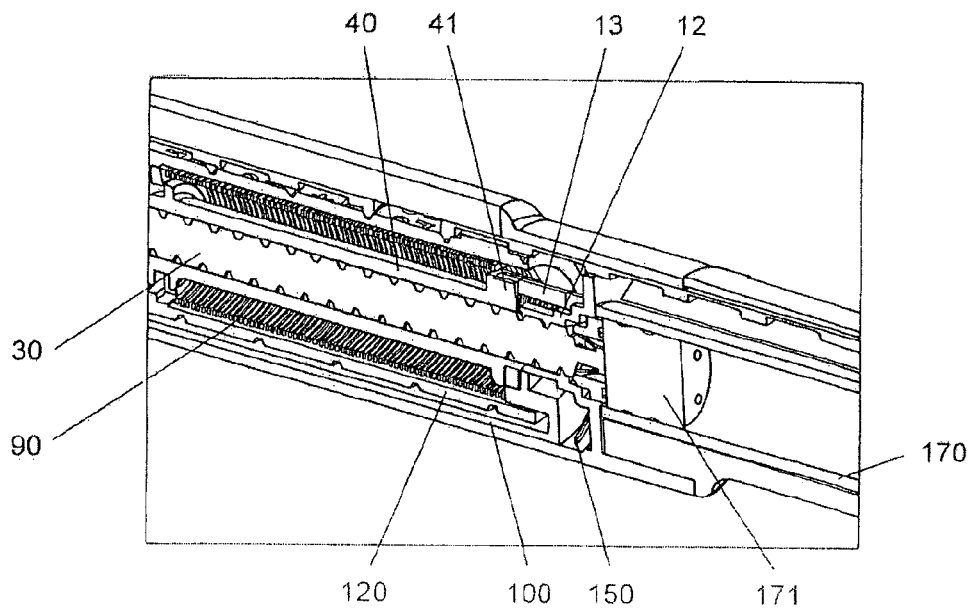
FIG. 9 shows an enlarged sectional view of a detail of the device of FIG. 1.

With the mechanism in a state in which a dose has been selected, the user is able to activate the mechanism to commence delivery of a dose. Delivery of a dose is initiated by the user depressing the dose button 70 at the proximal end of the device. FIGS. 7 and 8 show the device in the two positions dose button 70 in at rest condition (FIG. 7) and dose button 70 depressed (FIG. 8). When the dose button 70 is depressed, splines 71, 72 to the dial sleeve 60 and the dose button 70 are disengaged, rotationally disconnecting the dose selector 80 from the delivery mechanism so that the dose selector 80 does not rotate during dispense. In a preferred embodiment, the dose selector 80 is disconnected from the drive member 40 during dispense, when splines between the dose button and housing are engaged and splines between the dose button and dose indicator are disengaged. The dose button 70 acts on the locking arm 100, which travels axially disconnecting the splined tooth engagement 41, 101 to the driver 40. The driver 40 can now rotate and is driven by the torsion spring 90 via the dose indicator 120, dial sleeve 60 and clutch plate 130. Compression of the return spring increases frictional forces in the clutch helping to prevent it slipping during dispense and so ensure that the driver rotates the same amount as the dose indicator. In a preferred embodiment, this is still the case, but in addition to this, splines between the dose indicator and drive member are engaged during dispense to prevent relative rotation. Rotation of the driver 40 causes the lead screw 30 to rotate due to their splined engagement, and the lead screw 30 then advances due to its threaded engagement to the housing 10. The number sleeve rotation also causes the gauge element 110 to traverse axially back to its zero position whereby the zero dose abutment 122 stops the mechanism.

Tactile feedback during delivery is provided via a compliant cantilever beam 13 integrated into the housing 10, which interfaces axially with the spline teeth 41 of the driver 40, whereby the spline teeth spacing corresponds to the driver 40 rotation required for a single unit dispense. During dispense, as the driver 40 rotates, the spline features 41 engage with the clicker arm 13 to produce an audible click with each dose unit delivered. Delivery of a dose continues via the mechanical interactions described above while the user continues to depress the dose button 70.

If the user releases the dose button 70, the clutch spring 140 and the return spring 150 cooperate to return the dose button to its at rest position. The return spring 150 acts on the dose button 70 via the locking arm 100 so this is also translated axially. As the locking arm 100 returns towards its at rest position the splines 101 engage with the spline features 41 of the driver 40, rotationally constraining the driver 40 relative to the housing 10 and halting the delivery of the dose.

During delivery of a dose, the driver 40 and dial sleeve 60 rotate together, so that no relative motion in the nut 50 occurs. The nut 50 therefore travels towards its abutment on the driver 40 during dialling only.

Once the delivery of a dose is stopped, by the dose indicator 120 returning to the zero dose abutment, the user may release the dose button 70, which will re-engage the locking arm 100 spline teeth with the driver 40. The mechanism is now returned to the at rest condition.

It is possible to angle the spline teeth 41, 101 on either one or both of the driver 40 and locking arm 100 so that when the dose button 70 is released the re-engagement of the spline teeth fractionally 'backwinds' the driver 40 thereby removing the engagement of the dose indicator 120 to the gauge element 110 zero dose stop abutment 122. This removes the effect of clearances in the mechanism (for example due to tolerances) which could otherwise lead to slight advancement of the lead screw 30 and medicament dispense when the device is dialled for the subsequent dose (due to the dose indicator 120 zero dose stop 122 no longer restraining the mechanism and instead the restraint returning to the splines between the drive sleeve and locking arm 100.

Figure 4:
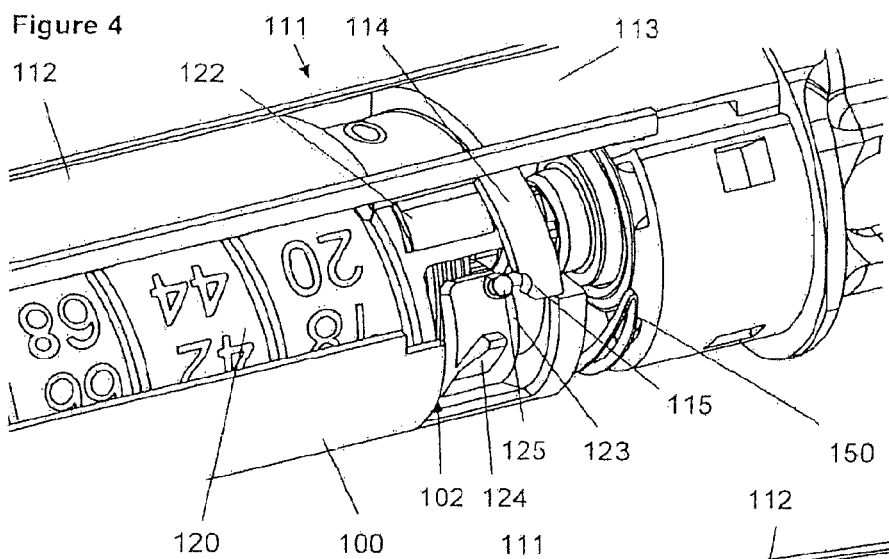
FIG. 4 shows an enlarged view of a detail of the device of FIG. 1.
Figure 5A:
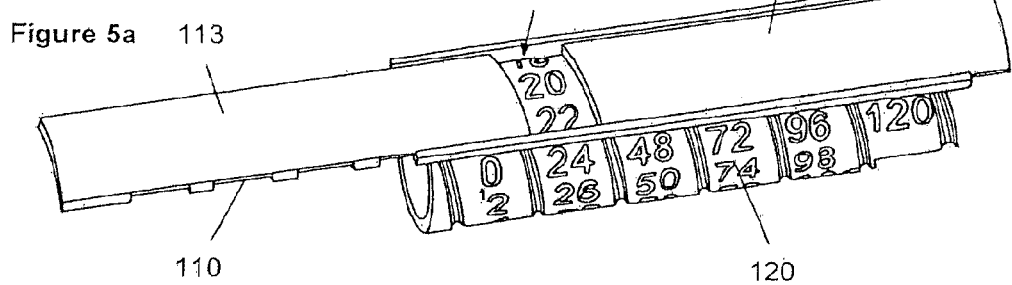
FIG. 5a shows an enlarged view of a detail of the device of FIG. 1.
Figure 5B:
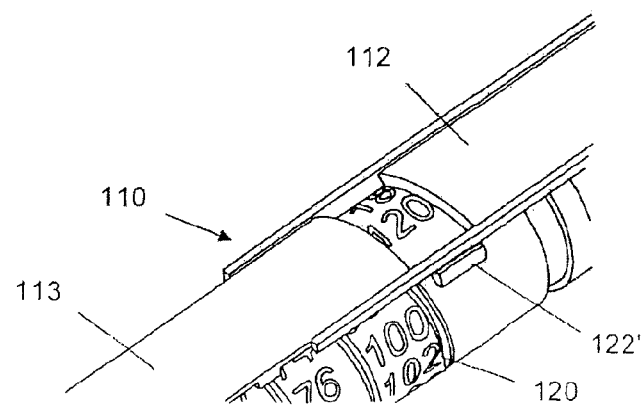
FIG. 5b shows an enlarged view of a detail of the device of FIG. 1.
Figure 5C:
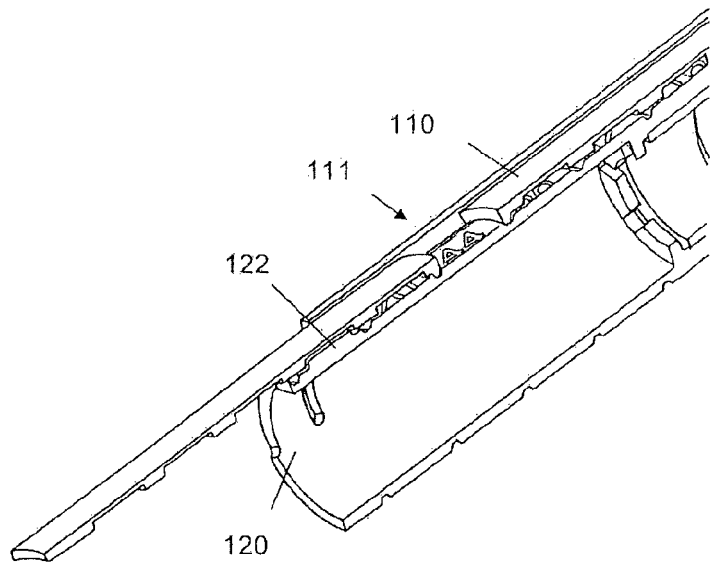
FIG. 5c shows an enlarged view of a detail of the device of FIG. 1.

At the end of dose, additional audible and/or tactile feedback is provided in the form of a click, distinct from the clicks provided during dispense, to inform the user that the device has returned to its zero position. This is achieved by the interaction of three components, namely the dose indicator 120, the gauge element 110 and the locking arm 100. This embodiment allows feedback to only be created at the end of dose delivery and not created if the device is dialled back to, or away from, the zero position. FIG. 4 shows the position of the features when a dose is dialled. It can be seen that the locking arm 100 does not contact the flexible arm 123 of the dose indicator 120 and therefore during dialling the flexible arm 123 is not deflected. However, during dose delivery, the locking arm 100 is in an axially advanced (distal) position whereby it deflects the flexible arm 123 of the number sleeve axially. As can be seen in FIG. 4, the locking arm 100 has a cut out or slot having a distal face 102, which interacts with a protrusion 124 on the arm 123 if the locking arm 100 is displaced in the distal direction upon depression of button 70. Thus, the flexible arm 123 on the dose indicator 120 is deflected axially by locking arm 100 only when the dose button 70 is depressed, i.e. during dose dispensing and not during dose setting or dose cancelling. As the dose indicator 120 returns to its zero position, the flexible arm 123 contacts with a further protrusion 125 the semi-flexible arm 114 of the gauge element 110. At the zero position, the flexible arm 123 over-rides the arm 114 of the gauge element 110 creating a distinctive click feedback. In the embodiment of FIG. 4, arm 114 has a recess 115 into which the protrusion 125 snaps to increase the audible and/or tactile feedback at the zero position.

A second embodiment is depicted in FIGS. 10 to 18. The general function of this device is similar to that of the first embodiment. Thus, identical or highly similar components are marked with the same reference numerals as with the first embodiment. As can be taken from the overview of the component parts in FIG. 10, this embodiment has a trigger 200 for displacing driver 40 by means of an internal actuation element, which is referred to as the trigger inner 210. The trigger 200 is pivotably held on the housing 10 by means of a trigger housing 220. In addition, an inner housing 190 and a grip cover 180 are provided. All components, except for the trigger 200 and the trigger housing 220, are located concentrically about a common principal axis of the mechanism.

The housing 10 provides location for the liquid medication cartridge 170, the mount points for the trigger housing 220, an interface to rigidly constrain the inner housing 190, a slot 11 through which the dose number on the dose indicator 120 can be viewed, and a feature, e.g. a circumferential groove, on its external surface to axially retain the dose selector 80.

A removable cap (not shown) may be provided to fit over the cartridge holder 20 of the housing 10 and may be retained onto the housing 10 via clips when the mechanism is not in use. When the cap is fitted onto the housing 10, a mechanical interlock may be created with the trigger 200, which prevents the trigger 200 from being depressed from its at rest position.

The lead screw 30 has an outer thread 31 and is rotationally constrained to the driver 40 via a splined interface. The interface comprises at least one longitudinal groove or track 32 and a corresponding protrusion or spline 44 of the driver 40. Similar to the first embodiment, when rotated, the lead screw 30 is forced to move axially relative to the driver 40, through a threaded interface with the housing 10.

The driver 40 extends from the interface with the dial sleeve 60 via the clutch plate 130 down to a splined tooth interface 41, 191 with the inner housing 190, which occurs on an axial abutment. This provides rotational constraint for the driver 40 during dose setting. As in the first embodiment, an end stop for the nut 50 is provided (not shown).

The nut 50 is located between the dial sleeve 60 and the driver 40. It is rotationally constrained to the dial sleeve 60, via a splined interface. It moves along a helical path relative to the driver 40, via a threaded interface, when relative rotation occurs between the dial sleeve 60 and driver 40. Again, the engagement of the nut 50 with the driver 40 and the dial sleeve 60 may be vice versa. Thus nut 50 is depicted as a half nut, but may have the form of a full nut.

The dial sleeve 60 is coupled to the driver 40 via a ratchet interface on the clutch plate 130, which occurs on an axial abutment. The ratchet which is formed by teeth 42, 131 provides a detented position between the dial sleeve 60 and driver 40 corresponding to each dose unit, and engages different ramped tooth angles during clockwise and anti-clockwise relative rotation.

The dose selector 80 is axially constrained to the housing 10. It is rotationally constrained, via a splined interface 81, 132, to the clutch plate 130. A grip cover 180 is rigidly constrained to the dose selector 80.

The torsion spring 90 is attached at one end to the inner housing 190 and at the other end to the dial sleeve 60. The torsion spring 90 is pre-wound upon assembly, such that it applies a torque to the dial sleeve 60 when the mechanism is at zero units dialled. The action of rotating the dose selector 80, to set a dose, rotates the dial sleeve 60 relative to the inner housing 190, and winds up the torsion spring 90.

The gauge element 110 is constrained to prevent rotation but allow axial translation relative to the housing 10 via a splined interface. It is also in threaded engagement to the dose indicator 120 such that rotation of the dose indicator 120 causes axial translation of the gauge element 110. The design and functions of the gauge window are the same as in the first embodiment.

The dose indicator 120 is rotationally constrained, via a splined interface, to the dial sleeve 60. They are constrained by the inner housing 190 to allow rotation but not translation. The dose indicator 120 is marked with a sequence of numbers, which are visible through the gauge element 110 and slot 11 in the housing 10, to denote the dialled dose of medicament.

Figure 14:
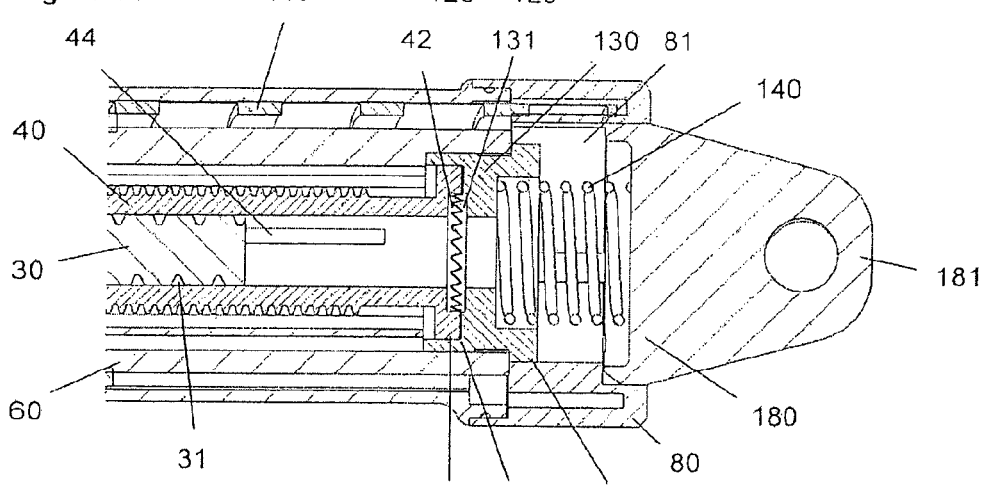
FIG. 14 shows an enlarged sectional view of a detail of the device of FIG. 10.

The clutch spring 140 is located between the clutch plate 130 and grip cover 180 and acts to force the clutch plate 130 and driver 40 towards the cartridge end of the mechanism. The ratchet teeth 61, 133 (actually spline features) are permanently engaged between the dial sleeve 60 and clutch plate 130. The clutch spring 140 biases the clutch plate 130 towards the cartridge end to engage splines 132, 81 on the inner surface of the dose selector 80. FIG. 14 shows the clutch plate 130 together with the proximal end of the device in more detail.

The bearing 160 is axially constrained to the lead screw 30 and acts on the bung within the liquid medicament cartridge 170.

The inner housing 190 is a tubular element which is rigidly constrained to the housing 10 and locks the driver 40 when the trigger 200 is not depressed by means of toothed interface 41, 191. Near its distal end, there is a clicker arm 192 (FIGS. 15a, b) interacting with the drive sleeve teeth 41 during dose dispensing to create an audible and/or tactile feedback.

The trigger 200 is constrained to pivot in the housing 10. When the trigger 200 is depressed, it acts on the trigger inner 210 causing the trigger inner 210 to translate axially thereby axially translating the driver 40 and disengaging the driver 40 from its splined tooth engagement to the inner housing 190. Actuation of the device by the trigger results in a low actuation force compared with devices where the user has to exert the dispensing force.

The trigger inner 210 a ring shaped element which is constrained to move axially when the trigger 200 is depressed. The trigger inner 210 has two protrusions 211 which extend in the proximal direction (FIG. 15a). The protrusions 211 that act on the driver 40 to disengage the driver 40 from the inner housing 190 when the trigger 200 is depressed (FIG. 15b).

The trigger housing 220 clips into the housing 10, and retains the trigger 200 within its pivot interface with the housing 10.

In the following, the functioning of the disposable drug delivery device and its components will be explained in more detail.

The user selects a variable dose of liquid medicament by rotating the dose selector 80 clockwise, which generates an identical rotation in the dial sleeve 60 and hence dose indicator 120. Rotation of the dial sleeve causes charging of the torsion spring 90, increasing the energy stored within it. As the dose indicator 120 rotates, the gauge element 110 translates axially due to its threaded engagement thereby showing the value of the dialled dose. As mentioned above, the gauge element 110 has flanges 112, 113 either side of the window 111 area which may have visual differentiation to provide additional feedback to the dialled/delivered dose value. The trigger mechanism also has an ergonomic tapered or flattened feature 181 on the Grip Cover 180 which is functionally part of the dial grip which aids users whilst dialling, especially if they have limited dexterity. The driver 40 is prevented from rotating, due to the engagement of its splined teeth 41 with the inner housing 190. Relative rotation must therefore occur between the clutch plate 130 and driver 40 via the ratchet interface 42, 131. The movement of the nut 50 and cancelling of a set dose is the same as explained for the first embodiment.

After a dose has been set as explained above for the first embodiment, the device is ready for dose dispensing. Delivery of a dose is initiated by the user depressing the trigger 200 on the side of the device. FIGS. 17 and 18 show the device in the two positions trigger 200 in at rest condition (FIG. 17) and trigger 200 depressed (FIG. 18). When the trigger 200 is depressed, the trigger acts on the trigger inner 210 moving it axially away from the cartridge 170. The trigger inner 210 acts on the driver 40 displacing it axially, i.e. the driver 40 moves the clutch plate 130 axially disengaging the clutch plate 130 from the dose selector 80. Then the drive sleeve spline teeth 41 disengage from the corresponding teeth 191 of inner housing 190. The driver 40 can now rotate and is driven by the torsion spring 90 via the dose indicator 120, dial sleeve 60 and clutch plate 130. Rotation of the driver 40 causes the lead screw 30 to rotate due to their splined engagement, and the lead screw 30 then advances due to its threaded engagement to the inner housing 190. During delivery of a dose, the driver 40 and dial sleeve 60 rotate together, so that no relative motion in the nut 50 occurs. The nut 50 therefore travels towards its abutment on the driver 40 during dialling only.

Delivery of a dose continues via the mechanical interactions described above while the user continues to depress the trigger 200. If the user releases the trigger 200, it returns to its at rest position and the driver 40 becomes rotationally constrained to the inner housing 190 so that delivery of a dose is halted.

The dose indicator 120 rotation also causes the gauge element 110 to traverse axially back to its zero position whereby the zero dose abutment 122 stops the mechanism. Once the delivery of a dose is stopped, by the dose indicator 120 returning to the zero dose abutment 122, the user may release the trigger 200, which will re-engage the inner housing spline teeth 191 with the drive sleeve teeth 41. The mechanism is now returned to the at rest condition.

Tactile feedback during delivery is provided via the clicker arm 192 integrated into the inner housing 190, which interfaces radially with the spline teeth 41 of the driver 40 when the trigger 200 is depressed and the driver 40 is in its axial dispense position, i.e. in its proximal position. The spline teeth 41 spacing corresponds to the driver 40 rotation required for a single unit dispense. During dispense, as the driver 40 rotates, the spline features 41 engage with the clicker arm 192 to produce an audible click with each dose unit delivered.

It is possible to angle the spline teeth 41, 191 on either one or both of the driver 40 and inner housing 191 so that when the trigger 200 is released the re-engagement of the spline teeth 41, 191 fractionally 'backwinds' the driver 40 thereby removing the engagement of the dose indicator 120 to the gauge element 110 zero dose stop 122 abutment. This removes the effect of clearances in the mechanism (for example due to tolerances) which could otherwise lead to slight advancement of the lead screw 30 and medicament dispense when the device is dialled for the subsequent dose (due to the dose indicator 120 zero dose stop 122 no longer restraining the mechanism and instead the restraint returning to the splines between the drive sleeve and inner housing 190.

At the end of dose, additional tactile feedback is provided in the form of a "click", distinctive from the "clicks" provided during dispense, to inform the user that the device has returned to its zero position via the interaction of three components, namely the dose indicator 120, the gauge element 110 and the trigger inner 210. This embodiment allows feedback to only be created at the end of dose delivery and not created if the device is dialled back to, or away from, the zero position. FIG. 16*a* shows the position of the features when a dose is dialled. It can be seen that a semi-flexible arm 123 of the dose indicator 120 does not contact a flexible arm 114 of the gauge element 110 and therefore during dialling the flexible arm 114 is not deflected, i.e. it passes over the semi-flexible arm 123 without interaction of these two arms. During dose delivery, the trigger 200 forces the trigger inner 210 axially so that towards the end of dose an arm 212 on the trigger inner 210 forces the flexible arm 114 on the gauge element 110 to deflect axially (FIG. 16*b*), such that as the mechanism returns to zero the flexible arm 114 contacts a protrusion 125 of the semi-flexible arm 123 of the dose indicator 120, creating a "click" as the mechanism reaches the zero stop position. The arm 114 may have on its radially inner side a protrusion or recess (not shown) for interaction with protrusion 125 on semi-flexible arm 123.

A third, alternative embodiment is shown in FIGS. 19 and 20. Similar to the first embodiment, the device of this third embodiment has a dose button 70 at its proximal end. The device features a translating dose indicator 120 for activation of the device during dose dispensing. In other words, the device utilises axial travel of the dose indicator 120 during dose button 70 actuation to release the driver 40 from its rotational lock with the housing 10. This reduces the outer diameter and length of the mechanism. FIG. 19 shows the device in an at rest position, whereas in FIG. 20 the dose button 70 is depressed. The functions of the components mainly correspond to the first embodiment.

In this third embodiment, the dose button 70 has an axial abutment with the dose indicator 120. Due to the length of the dose indicator 120, the separate dial sleeve of the first embodiment is omitted. In its distal region, the dose indicator 120 acts against a separate locking arm 230 which is splined to the housing 10 and has teeth for engaging corresponding teeth 41 of driver 40. Therefore, as the dose indicator 120 moves axially when the dose button 70 is depressed, the locking arm 230 is forced to move axially disengaging it from the driver 40 and allowing the torsion spring 90 to deliver the dose. Similarly, when the dose button 70 is released, the dose indicator 120 and locking arm 230 return to their original axial position, under the action of the axial spring 240, and the driver 40 is again locked against rotation.

Since the gauge element 110 is threaded to the dose indicator 120, it moves axially with the dose indicator 120 when the dose button 70 is depressed and released and therefore the gauge element 110 and Lens or slot 11 of the housing 10 remain aligned to the dose indicator 120 at all times so that the correct dose is displayed.

An additional spring 240 acts on the distal end of dose indicator 120 biasing the mechanism in the at rest position, i.e. the proximal position of the number sleeve. For manufacturing reasons, the driver 40 may comprise two rigidly fixed component parts as indicated in FIGS. 19 and 20. The nut 50 is located between the driver 40 and the (extended) dose indicator 120.

Although the dose indicator 120 translates axially upon actuation of the dose button 70, there is no axial movement of the dose indicator 120 during dose setting nor during dose dispensing.

As can be taken from the above description of the three embodiments, significant features and advantages of the invention include:

The set and/or remaining dose is displayed through a window that moves axially within the device—the "gauge" feature. This provides additional visual dose progress feedback. This feedback can be enhanced if either side of this window 111, i.e. flanges 112, 113, has features such as separate colours and/or markings.

The dose indicator 120 does not translate helically in any embodiment.

The second embodiment has a large user friendly dose selector 80 profile with grip cover 180 to aid dose setting. This is only feasible if there is no button on the end.

The end button mechanisms of the first and third embodiments have an oversized dose selector 80 to aid dose setting.

An end-of-dose click is incorporated in each mechanism that operates during dose delivery but not dose setting or cancellation.

An alternative third embodiment exists for the end button mechanism of the first embodiment whereby the dose indicator 120 moves axially during dose button 70 actuation and release, but not during dose delivery.

An alternative fourth embodiment of an injection device 1 is shown in FIG. 21 in an exploded view. The injection device comprises 19 components, excluding the liquid medicament cartridge. In more detail, the device comprises a housing 410, which includes a main housing 411, a proximal cap 412 and a cartridge holder 413, a dial grip 420, a dispense button 430, a dial tube 440, a last dose nut 450, a sleeve-like clicker 460, a dispense spring 470, a dose indicator (dial sleeve) 480, a sliding gauge 490, a drive member 500 including a drive sleeve 501 and a drive tube 502, a motor spring 510, a storage spool 520, a piston rod (lead screw) 530 with a bearing 531, a lens (not shown) and a cap (not shown). Most of the components are located concentrically about one of two principle axes I and II of the mechanism as shown in FIG. 22.

The piston rod 530 is located within the housing 510. The drive member 500 is permanently coupled to the piston rod 530 and the drive member 500 is axially movable between a dose setting position, in which the drive member 500 is rotationally constrained to the housing 410, and a dose dispensing position, in which the drive member 500 is rotationally de-coupled from the housing 410. The power reservoir 510 for driving the drive member 500 comprising a reverse wound flat spiral spring as a power reservoir having a first end attached to the first spool 520 and a second end attached to a second spool, which is axially and rotationally constrained to drive member 500. For example, the second spool is an integral part of drive sleeve 501. In the embodiment shown in the Figures, the second end of the spring 510 comprises a portion of reduced width and a free end portion having an increased width compared with the portion of reduced width, wherein the drive member 500, in more detail drive sleeve 501, comprises a cylindrical spool portion having an axial slot 503 and an adjacent narrow recess.

Preferably, the dose indicator 480 is axially constrained to the housing 410 and rotates during dose setting relative to the housing in either a first direction (increasing a dose) or a second opposite direction (decreasing a dose) and it rotates during dose dispensing relative to the housing in the second opposite direction. The gauge element 490 is at least partly interposed between the housing 410 and the dose indicator 480 and at least partly visible through at least one aperture or window of the housing 410. Further, the gauge element 490 is axially guided within the housing 410 and in threaded engagement with the dose indicator 480 such that rotation of the dose indicator 480 causes an axial displacement of the gauge element 490. The housing 410 has an aperture or window and the gauge element 490 has a further aperture or window, which is positioned with respect to the aperture or window of the housing such that at least a part of the dose indicator 480 is visible through the apertures or windows.

In particular, the apertures may be located on the main housing 411 in a location which is visible to the user during dispense of a dose. This may be close to the distal end of the device. Particularly this may be a location in which the number display of the dose indicator 480 could not feasibly be located. There may also be a plurality of gauge apertures. In particular there may be two gauge apertures, located on opposite sides of the device This increases the visibility of the analog gauge feature for users with a preference for left handed operation, or those users with a preference to hold the device with an alternative grip. The analog gauge is particularly beneficial as an indicator of the dose position of the device during dispense of a dose. During dispense of a dose the number digit display may be changing too quickly for individual dose position markings to be legible. It may therefore be difficult for the user to understand the rate at which the dose is being dispensed, and the amount of medicament still to be dispensed. The axial motion of the analog gauge, which increasingly covers a further surface as a dose is dispensed, gives a simple visible indicator of the dispense rate and the amount of medicament still be to dispensed during the dispense event.

The injection device comprises a limiter mechanism defining a maximum settable dose and a minimum settable dose. The limiter mechanism may comprise a first rotational stop on the dose indicator 480 and a first counter stop on the gauge element 490, which abut in the minimum dose (zero) position, and a second rotational stop on the dose indicator 480 and a second counter stop on the gauge element 490, which abut in the maximum dose position.

The dispense button 430 is axially displaceable and located surrounded by the dial grip 420 which is axially constrained to the housing 410. The clicker sleeve 460 is rotationally constrained to the housing 410 and is axially displaceable relative to the housing between a proximal dose setting position and a distal dose dispensing position. Further, the clicker sleeve 460 comprises teeth releasably engaging corresponding teeth of the dial sleeve 440 which is rotatable during dose setting. The dose indicator 480 may comprise a flexible clicker arm, which is displaceable by the clicker sleeve 460 in a first direction and only during dose dispensing when the device reaches its minimum dose (zero) position in a second, opposite direction by a protruding section of the gauge element 490.

The injection device may further comprise a last dose protection mechanism for preventing the setting of a dose, which exceeds the amount of liquid left in a cartridge. This last dose protection mechanism comprises the nut member 450 located interposed between the clicker sleeve 460 and the dial sleeve 440.

In the injection device the first spool 520 is located concentrically with the piston rod 530 on the first longitudinal axis I, and the second spool, i.e. the drive sleeve 501, is located on a second longitudinal axis II, wherein the first longitudinal axis I is parallel to and spaced from the second longitudinal axis II. As mentioned above, the drive member 500 may comprise the drive tube 502 which is rotatable about the first longitudinal axis I and the drive sleeve 501 which is rotatable about the second longitudinal axis II. The drive sleeve 501 is axially movable between the dose setting position, in which the drive sleeve 501 is rotationally constrained to the housing 410, and the dose dispensing position, in which the drive sleeve 501 is rotationally de-coupled from the housing 410. The drive tube 502 may be permanently rotationally coupled to the drive sleeve 501 or at least if the drive sleeve 501 is in its dose dispensing position.

A clutch 483, 505 is provided interposed between the dose indicator 480 and the drive member 500, wherein the clutch 483, 505 allows relative rotational movement between the dose indicator 480 and the drive member 500 during dose setting and prevents relative rotational movement between the dose indicator 480 and the drive member 500 during dose dispensing. As shown in FIG. 21, the clutch comprises a ring of teeth 505 on the distal side of drive sleeve 501 and inner splines 483 on the dose indicator. The drive sleeve 501 further has a ring of teeth 506 at its proximal end which mesh with corresponding teeth on the drive tube 502. In addition, teeth 506 couple the drive sleeve 501 rotationally to the housing in the (proximal) dose setting position of the drive sleeve 501.

Each of the above features is independent from the other features and independent from the internal functions of the other component parts, like the clutch, the ratchets, the clickers, the dose display or the actuation means.

A further common feature of all embodiments is that the device has no dial extension, i.e. the length of the device is the same whether a dose has been dialled or not. In addition, the dose selector 80 does not spin during dispense and it is shaped (either flattened or large diameter) to make dialling easier. The gauge element 110 provides qualitative feedback to the user on the progress of the dose. This is especially important for visually impaired users who may find it difficult to identify individual numbers or symbols on the number sleeve. All of which should provide a significant ergonomic benefit to the user.

The invention claimed is:

1. An injection device comprising:
    a housing;
    a dose setting member operatively connected to a dose indicator positioned within the housing, the dose setting member and the dose indicator being configured to cooperate to set a dose to be ejected from the injection device during dose setting, and the dose indicator being configured to rotate within the housing and relative to the housing during the dose setting;
    a gauge element rotationally constrained to the housing and axially displaceable relative to the housing;
    a limiter mechanism defining a minimum settable dose, the limiter mechanism being formed at least in part by the gauge element and the dose indicator;
    a piston rod having a threaded outer surface with a drive track extending along a longitudinal direction and along the threaded outer surface of the piston rod;
    a drive member engaging at least part of the drive track of the piston rod and being releasably coupled to the dose indicator, the drive member being adapted to drive and rotate the piston rod during dose dispensing, wherein the housing comprises a threaded portion engaged with the threaded outer surface of the piston rod such that rotation of the piston rod axially displaces the piston rod relative to the housing; and
    a clutch arranged between the drive member and the dose indicator, the clutch being configured to enable relative rotation between the drive member and the dose indicator during the dose setting and being configured to rotationally constrain the drive member and the dose indicator during the dose dispensing.

2. The injection device of claim 1, wherein the limiter mechanism further defines a maximum settable dose and comprises a rotational stop on the dose indicator and a counter stop on the gauge element, the rotational stop being configured to abut counter stop when the dose indicator is in a maximum dose position corresponding to the maximum settable dose.

3. The injection device of claim 1, wherein the gauge element is in threaded engagement with the dose indicator such that rotation of the dose indicator axially displaces the gauge element relative to the dose indicator and relative to the housing.

4. The injection device of claim 3, wherein the dose indicator is adapted to rotate relative to the housing, to remain translationally fixed relative to the housing, and to remain within the housing during the dose setting and during dose dispensing.

5. The injection device of claim 1, wherein the gauge element is adapted to translate relative to the housing, to remain rotationally fixed relative to the housing, and to remain within the housing during the dose setting and during dose dispensing.

6. The injection device of claim 1, wherein:
    the dose indicator comprises a sequence of numbers,
    the gauge element defines an aperture, and
    the dose indicator is located radially inwards of the gauge element such that at least one number of the sequence of numbers on the dose indicator is visible through the aperture.

7. The injection device of claim 1, further comprising a resilient member configured to be strained during the dose setting to provide a force to eject the dose from the injection device.

8. The injection device of claim 7, comprising a button located on a proximal end of the housing, the button being actuatable to release the resilient member.

9. The injection device of claim 7, further comprising a trigger located on a lateral side of the housing, the trigger being actuatable to release the resilient member.

10. The injection device of claim 1 comprising a last dose protection mechanism to inhibit setting of an excess dose exceeding an amount of liquid remaining in a cartridge loaded in the housing.

11. The injection device of claim 10, wherein the last dose protection mechanism comprises a nut member located between the drive member and a rotatable component configured to rotate relative to the housing during the dose setting and the dose dispensing.

12. The injection device of claim 11, wherein the rotatable component comprises the dose indicator or a dial sleeve rotationally constrained to the dose indicator during the dose setting and the dose dispensing.

13. The injection device of claim 1, further comprising:
    a first clicker configured to produce a first feedback during at least one of the dose setting and dose dispensing, the first feedback being audible and/or tactile; and
    a second clicker configured to produce a second feedback during the dose dispensing when the injection device reaches a minimum settable dose position, the second feedback being audible and/or tactile and being distinct from the first feedback.

14. The injection device of claim 1, further comprising a cartridge containing a medicament.

15. The injection device of claim 1, wherein a thread of the dose indicator is a female thread, and a thread of the gauge element is a male thread.

16. The injection device of claim 1, wherein the limiter mechanism comprises a first rotational stop on the dose indicator and a first counter stop on the gauge element, the first rotational stop being configured to abut the first counter stop when the dose indicator is in a minimum dose position corresponding to the minimum settable dose.

17. The injection device of claim 16, wherein the first rotational stop is a first hard stop positioned at an end of a thread of the dose indicator, and the first counter stop is a second hard stop positioned at an end of a thread of the gauge element.

18. A method of dispensing a dose to be ejected from an injection device, the method comprising:
    setting the dose by rotating a dose indicator of a limiting mechanism to set the dose between a minimum settable dose and a maximum settable dose and to cause axial displacement of a gauge element of the limiting mechanism relative to the dose indicator, the minimum settable dose and the maximum settable dose being defined by the limiting mechanism, wherein the dose indicator is positioned within a housing of the injection device; and dispensing the dose from the injection device,
wherein during the setting of the dose, a clutch enables relative rotation between a drive member of the injection device and the dose indicator, and during the dispensing of the dose, the clutch constrains rotation of the drive member and the dose indicator, the clutch being arranged between the drive member and the dose indicator,
wherein the drive member engages at least part of a drive track of a piston rod of the injection device and is releasably coupled to the dose indicator, the drive member being adapted to drive and rotate the piston rod during the dispensing of the dose
wherein the piston rod has a threaded outer surface with the drive track extending along a longitudinal direction and along the outer surface of the piston rod, and
wherein the housing comprises a threaded portion engaged with the threaded outer surface of the piston rod such that rotation of the piston rod axially displaces the piston rod relative to the housing.

19. The method of claim 18, wherein:
rotating the dose indicator comprises rotating the dose indicator in a first rotational direction to translate the gauge element in a first translational direction and to increase the dose toward the maximum settable dose, and rotating the dose indicator further comprises rotating the dose indicator in a second rotational direction to translate the gauge element in a second translational direction to decrease the dose toward the minimum settable dose.

20. The method of claim 18, wherein rotating the dose indicator comprises rotating the dose indicator while the dose indicator is axially constrained to a housing of the injection device and while the gauge element is rotationally constrained relative to the housing.

21. The method of claim 18, wherein the dose indicator is located radially inwards of the gauge element such that a portion of the dose indicator is visible through a window defined by the gauge element.

* * * * *

UNITED STATES PATENT AND TRADEMARK OFFICE
CERTIFICATE OF CORRECTION

PATENT NO. : 10,688,248 B2
APPLICATION NO. : 14/783481
DATED : June 23, 2020
INVENTOR(S) : Matthew Meredith Jones and Simon Lewis Bilton Page 1 of 1

It is certified that error appears in the above-identified patent and that said Letters Patent is hereby corrected as shown below:

In the Claims

Column 25, Line 50, Claim 2, after "abut", insert -- the --

Signed and Sealed this
Eleventh Day of August, 2020

Andrei Iancu
*Director of the United States Patent and Trademark Office*